(12) United States Patent
Chappo

(10) Patent No.: US 10,680,034 B2
(45) Date of Patent: Jun. 9, 2020

(54) IMAGING DETECTOR MODULE ASSEMBLY

(71) Applicant: KONINKLIJKE PHILIPS N.V., Eindhoven (NL)

(72) Inventor: Marc Anthony Chappo, Elyria, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/245,286

(22) Filed: Jan. 11, 2019

(65) Prior Publication Data
US 2019/0165012 A1 May 30, 2019

Related U.S. Application Data

(62) Division of application No. 15/304,545, filed as application No. PCT/IB2016/050059 on Jan. 7, 2016, now Pat. No. 10,217,790.

(Continued)

(51) Int. Cl.
*H01L 23/00* (2006.01)
*H01L 27/146* (2006.01)
(Continued)

(52) U.S. Cl.
CPC ...... *H01L 27/1469* (2013.01); *H01L 23/3675* (2013.01); *H01L 24/14* (2013.01);
(Continued)

(58) Field of Classification Search
CPC ..... H01L 23/3675; H01L 23/48; H01L 23/52; H01L 24/14; H01L 24/16; H01L 24/81;
(Continued)

(56) References Cited

U.S. PATENT DOCUMENTS 6,291,267 B1 * 9/2001 Dore ............... H01L 21/563
257/E21.503
6,510,195 B1 1/2003 Chappo
(Continued)

FOREIGN PATENT DOCUMENTS

JP 11166976 6/1999

OTHER PUBLICATIONS

Tamura, et al., "X-Ray Detector and X-Ray CT Device", Jun. 22, 1999, machine translation of JP 11-166976 obtained Sep. 13, 2017, pp. 1-13.

*Primary Examiner* — Natalia A Gondarenko
(74) *Attorney, Agent, or Firm* — Larry Liberchuk

(57) ABSTRACT

A module assembly device (402) is configured for assembling a module assembly (114) for a detector array (110) of an imaging system (100). The module assembly device includes a base (400) having a long axis (401). The module assembly device further includes a first surface (406) of the base and side walls (408) protruding perpendicular up from the first surface and extending in a direction of the long axis along at least two sides of the base. The first surface and side walls form a recess (404) configured to receive the module substrate on the surface and within the side walls. The module assembly device further includes protrusions (403) protruding from the side walls in a direction of the side walls. The protrusions and side walls interface forming a ledge which serves as a photo-detector array tile support (410) configured to receive the photo-detector array tile (118) over the ASIC and the module substrate.

12 Claims, 15 Drawing Sheets

Related U.S. Application Data

(60) Provisional application No. 62/103,785, filed on Jan. 15, 2015.

(51) Int. Cl.
    *H01L 27/00* (2006.01)
    *H01L 23/367* (2006.01)
    *H01L 31/00* (2006.01)
    *H01L 31/18* (2006.01)
    *H05K 1/18* (2006.01)
    *H05K 3/34* (2006.01)
    *A61B 6/03* (2006.01)
    *A61B 6/00* (2006.01)

(52) U.S. Cl.
    CPC .............. *H01L 24/16* (2013.01); *H01L 24/81* (2013.01); *H01L 27/14618* (2013.01); *H01L 27/14661* (2013.01); *H05K 1/18* (2013.01); *A61B 6/032* (2013.01); *A61B 6/4233* (2013.01); *H01L 27/14663* (2013.01); *H01L 2224/131* (2013.01); *H01L 2224/14131* (2013.01); *H01L 2224/14135* (2013.01); *H01L 2224/16145* (2013.01); *H01L 2224/81815* (2013.01); *H05K 3/3436* (2013.01); *H05K 2201/1053* (2013.01); *H05K 2201/10151* (2013.01)

(58) Field of Classification Search
    CPC ......... H01L 27/14618; H01L 27/14661; H01L 27/14663; H01L 27/1469; H01L 2224/81815; H01L 2224/14135; H01L 2224/131; H01L 2224/14131; H01L 2224/16145; H01L 2224/85801; H01L 2224/86815; H01L 2224/92122; H01L 2224/80; H01L 2224/81; H01L 2224/81801; H01L 2224/838; H01L 2224/83815; H01L 2224/84801; H01L 2224/84815; H01L 2224/8536; H01L 2225/1058; H01L 2225/1076; H01L 2225/1088; H01L 2225/1011; H01L 31/0216; H01L 31/0232; H01L 31/02325; H01L 31/054; H05K 2201/1053; H05K 2201/10151; H05K 3/3436; H05K 1/18; A61B 6/032; A61B 6/4233
    USPC ............... 257/432, 433, 447, 448, 777, 778, 257/E25.032, E27.133, E31.127; 438/109, 108, 107, 110, 126, 127, 118
    See application file for complete search history.

(56) References Cited

U.S. PATENT DOCUMENTS

| | | | |
|---|---|---|---|
| 7,002,254 B2 * | 2/2006 | Harper | H01L 25/0657 257/777 |
| 7,301,214 B2 | 11/2007 | Sekine | |
| 7,550,811 B2 * | 6/2009 | Kobayashi | H01J 37/224 257/431 |
| 7,977,643 B2 | 7/2011 | Weinberg | |
| 8,710,448 B2 | 4/2014 | Luhta | |
| 8,816,287 B2 | 8/2014 | Weinberg | |
| 9,151,668 B1 | 10/2015 | Nagarkar | |
| 2004/0164390 A1 * | 8/2004 | Wang | H01L 23/13 257/686 |
| 2004/0217485 A1 * | 11/2004 | Chung | H01L 21/563 257/778 |
| 2005/0139757 A1 | 6/2005 | Iwanczyk | |
| 2005/0253213 A1 | 11/2005 | Jiang | |
| 2006/0035415 A1 | 2/2006 | Wood | |
| 2006/0244153 A1 * | 11/2006 | Shibayama | H01L 27/14618 257/777 |
| 2008/0011959 A1 | 1/2008 | Thorne | |
| 2010/0309640 A1 | 12/2010 | Schlomann | |
| 2010/0327173 A1 | 12/2010 | Woychik | |
| 2013/0264483 A1 | 10/2013 | Abenaim | |
| 2017/0098625 A1 | 4/2017 | Takeda | |

\* cited by examiner

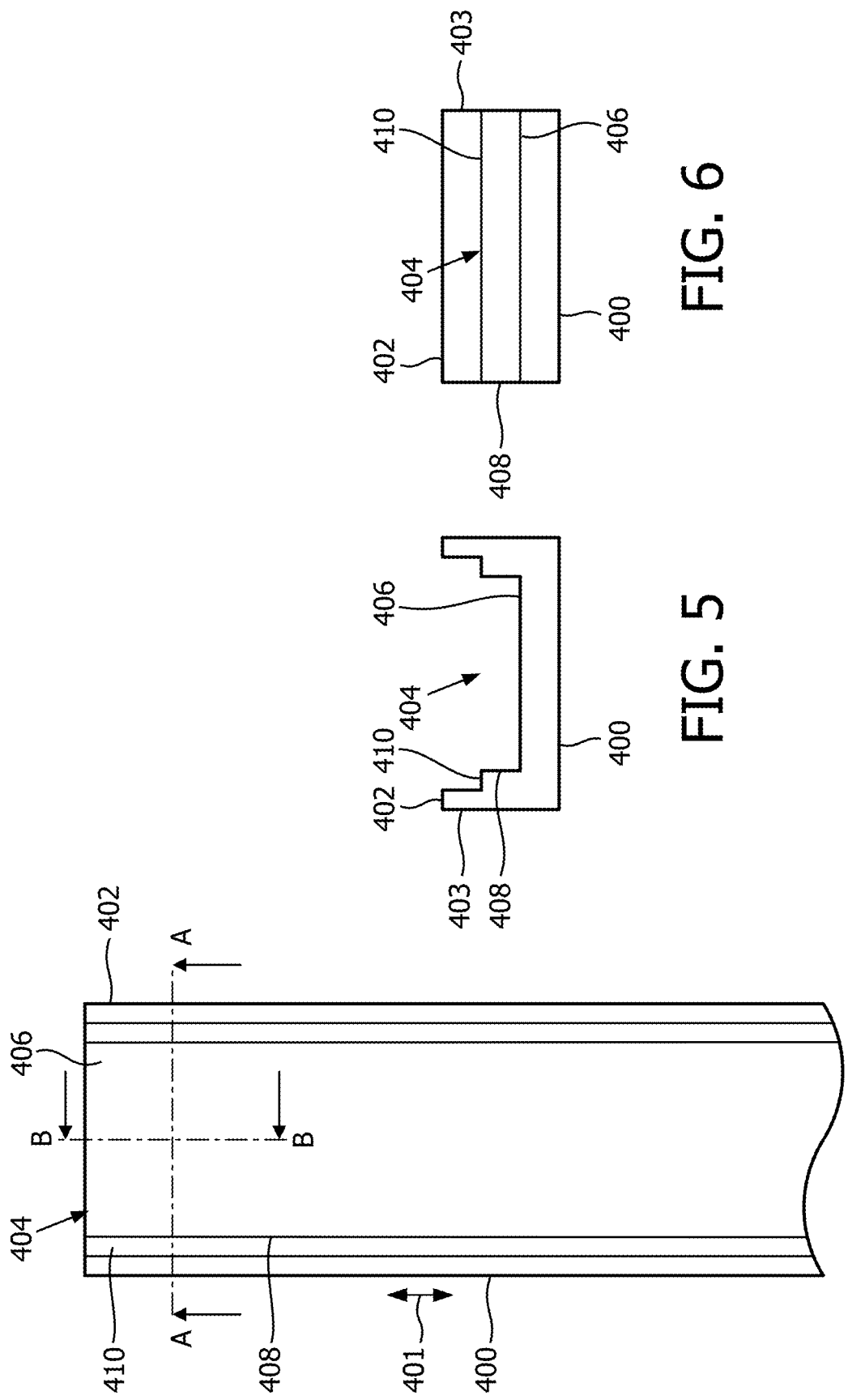

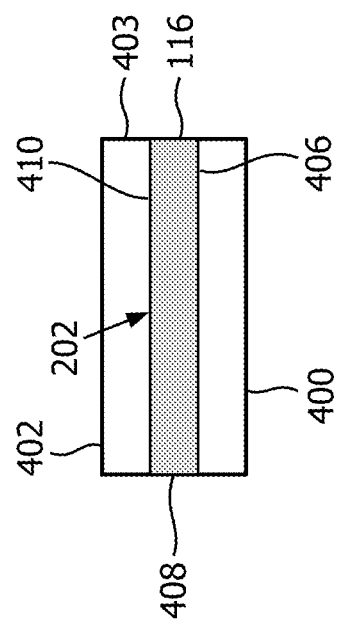
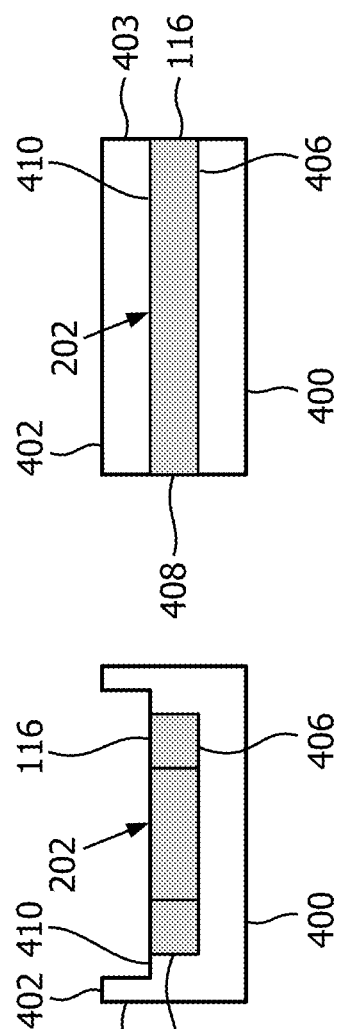
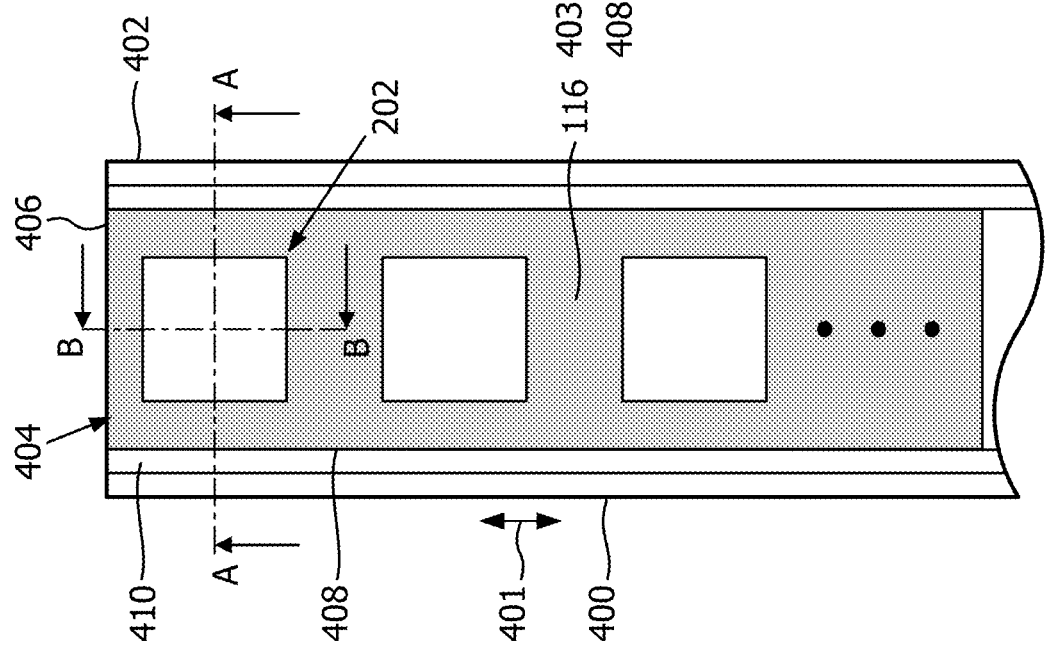

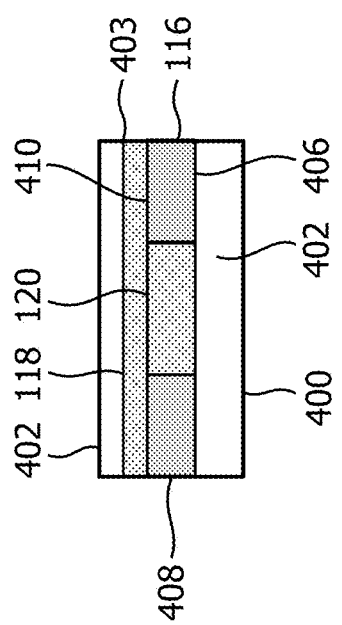
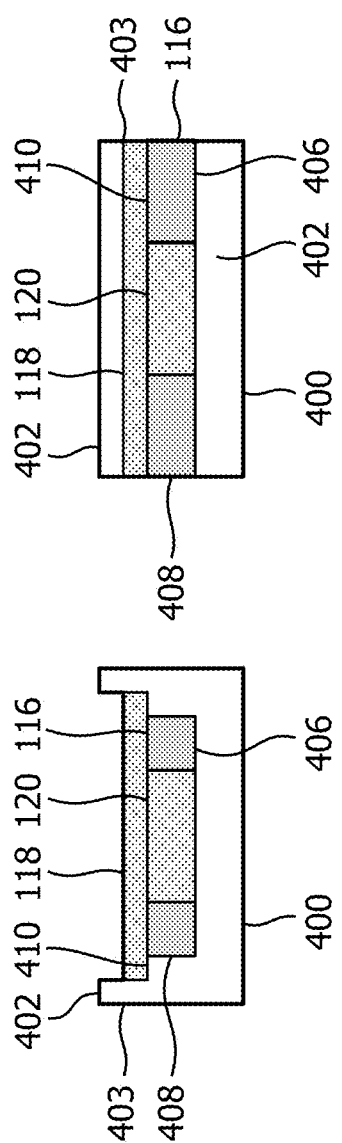
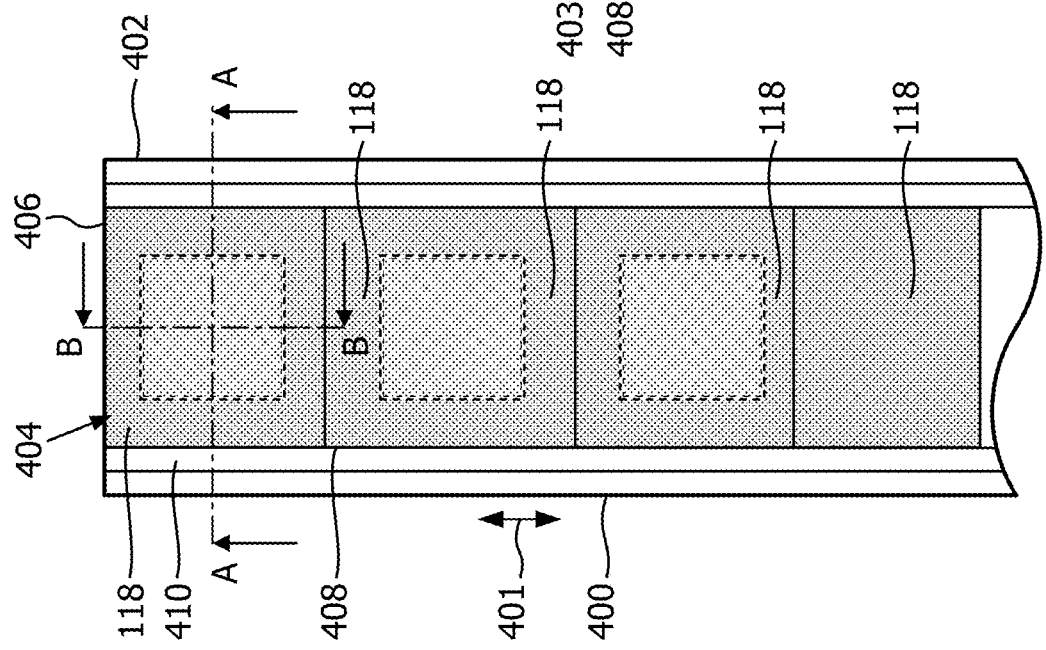

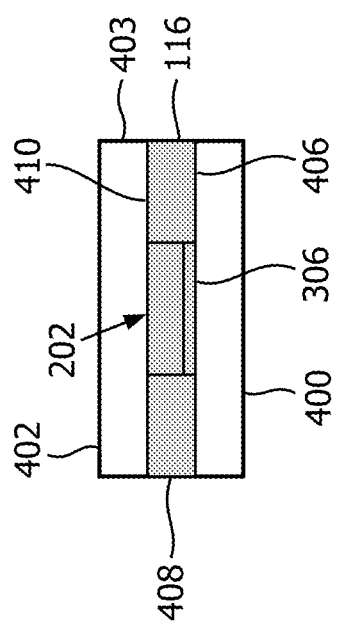
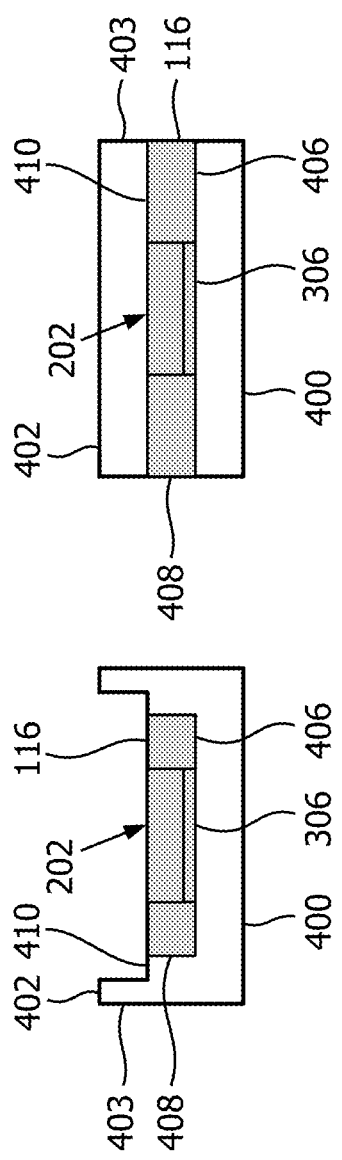
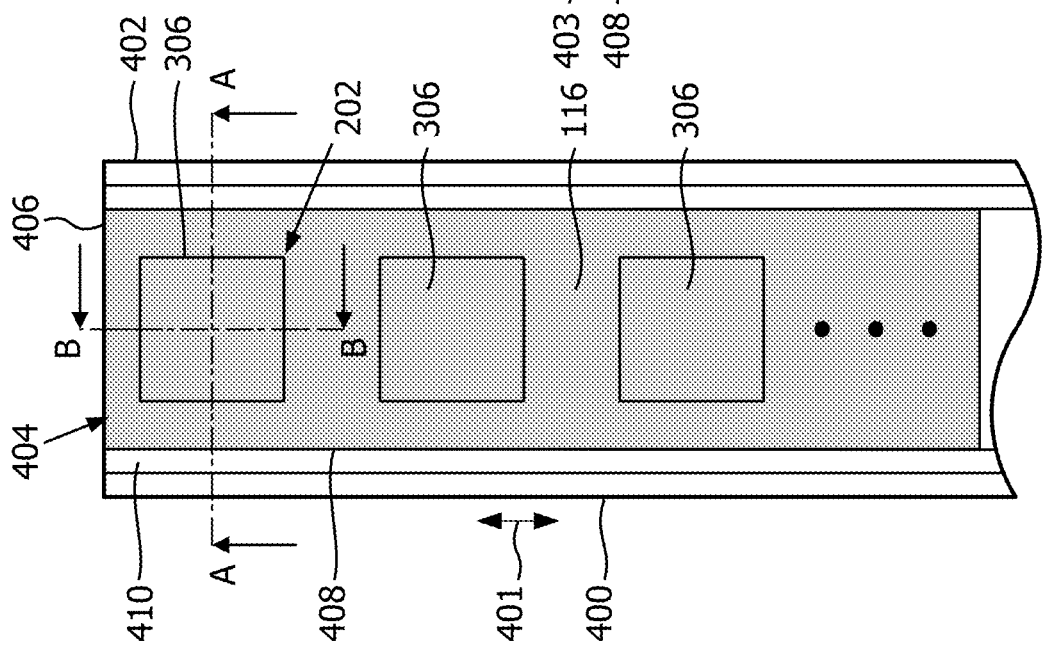

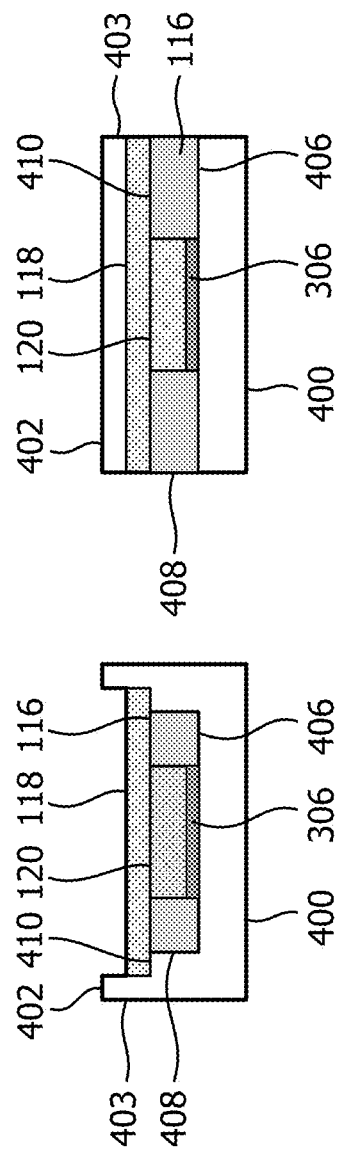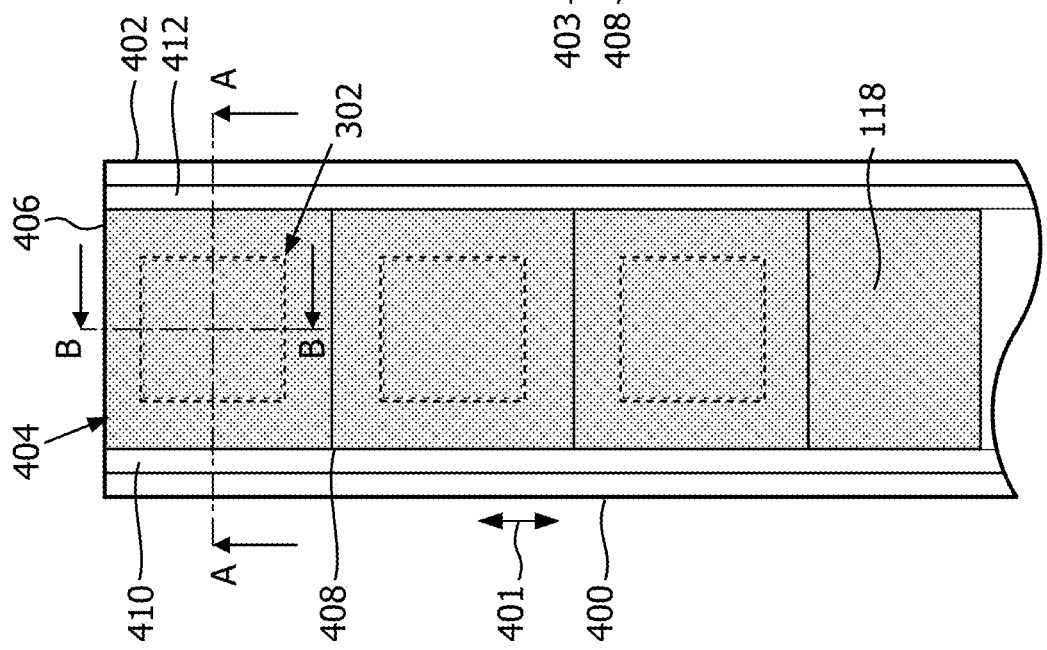
FIG. 19  FIG. 20  FIG. 21

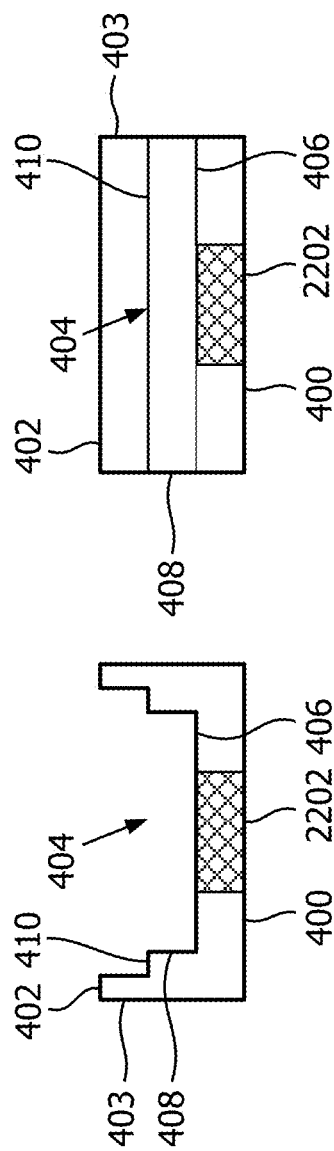
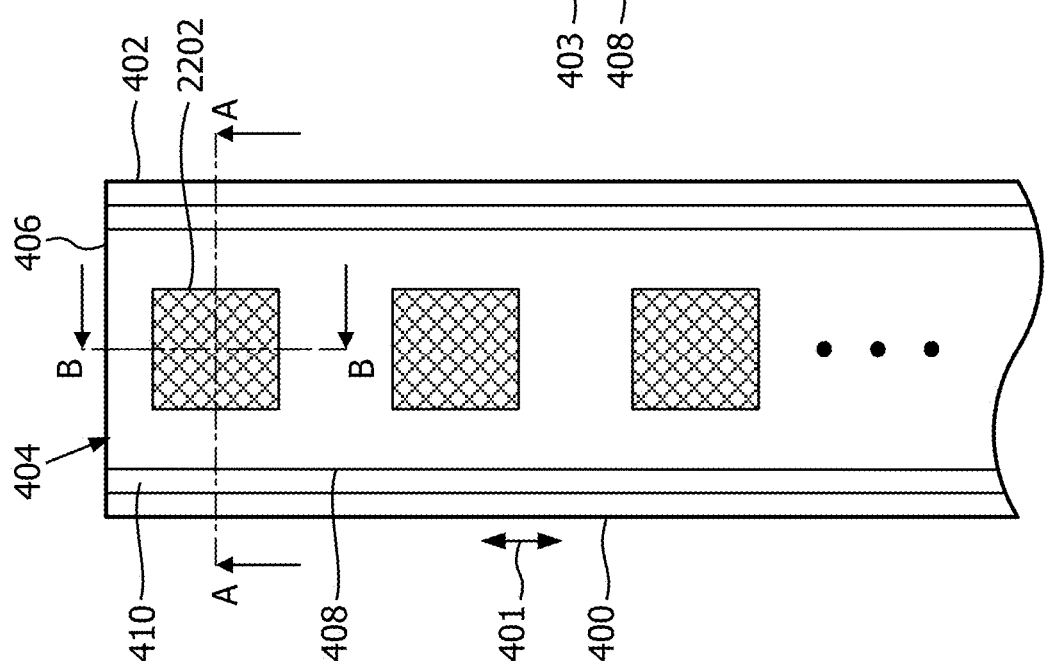

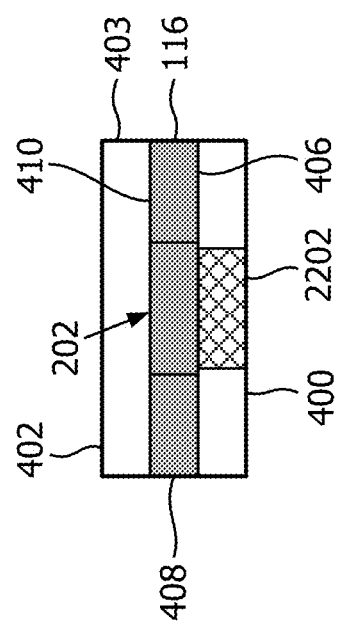
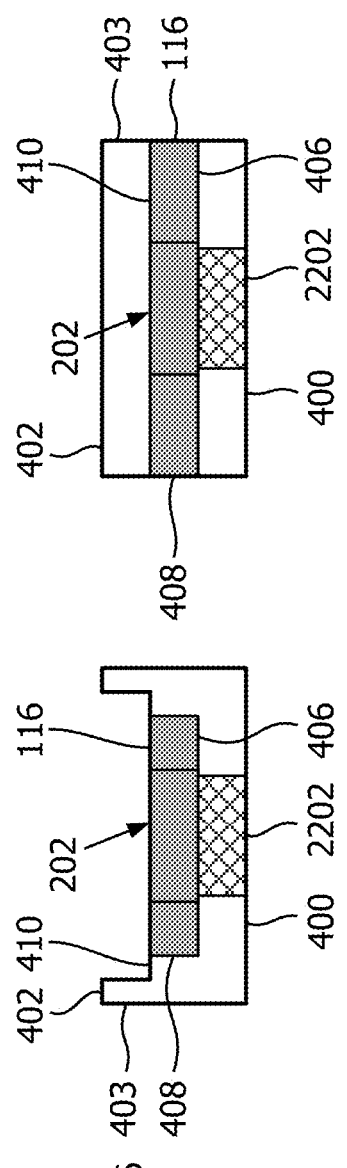
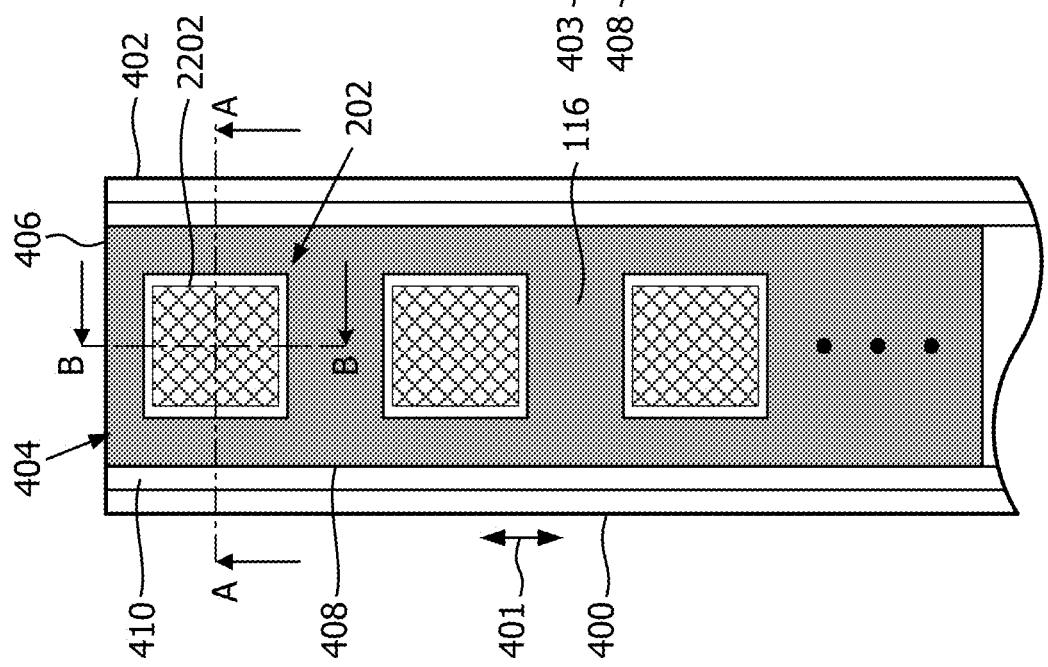

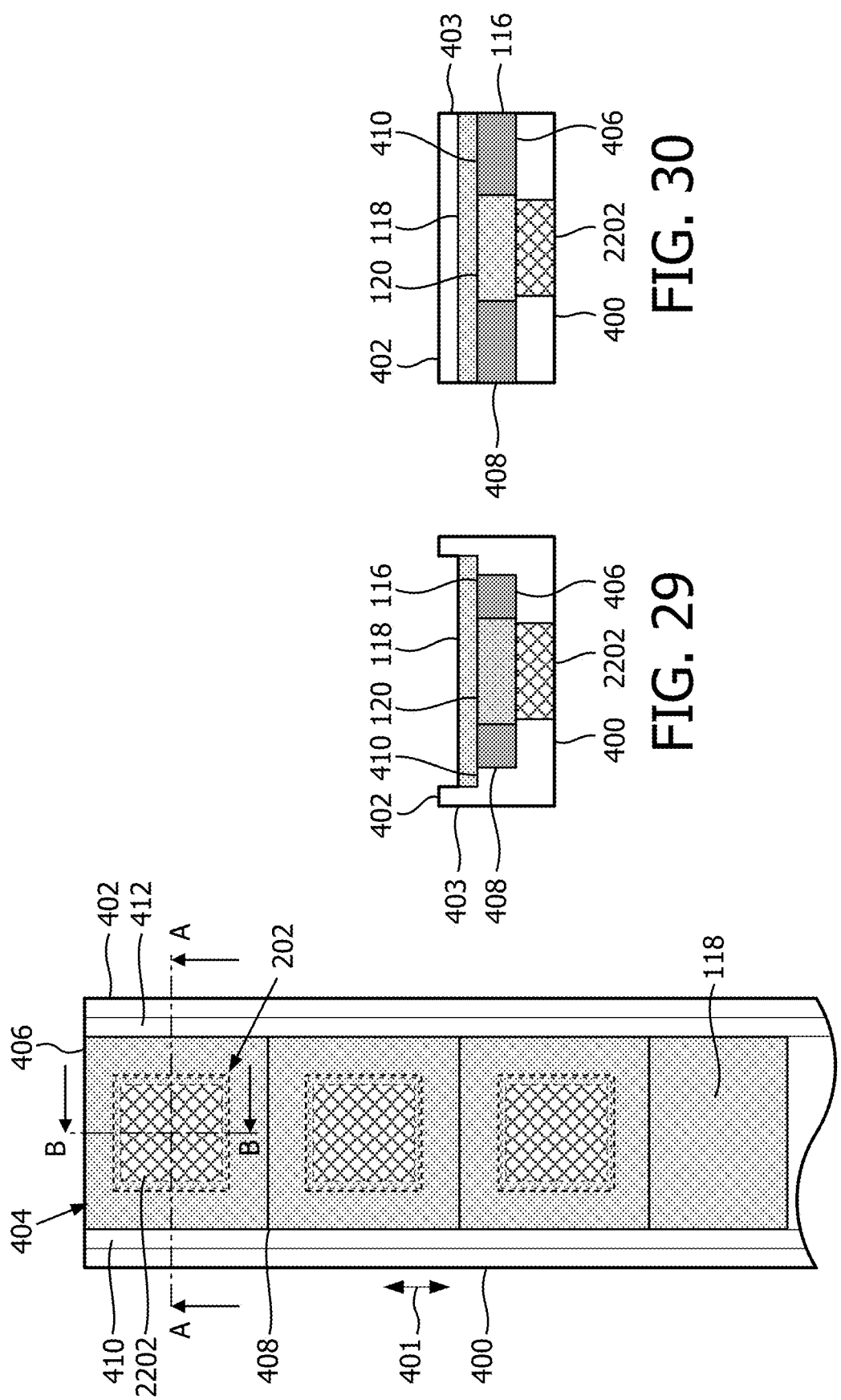

IMAGING DETECTOR MODULE ASSEMBLY

CROSS REFERENCE TO RELATED APPLICATIONS

This application is a divisional of U.S. patent application Ser. No. 15/304,545 filed Oct. 17, 2016, which is the U.S. National Phase application under 35 U.S.C. § 371 of International Application No. PCT/IB2016/050059, filed Jan. 7, 2016, published as WO 2016/113647 on Jul. 21, 2016, which claims the benefit of U.S. Provisional Patent Application No. 62/103,785 filed Jan. 15, 2015. These applications are hereby incorporated by reference herein.

FIELD OF THE INVENTION

The following generally relates to an imaging detector and more particularly an imaging detector module assembly, and is described in connection with computed tomography (CT). However, the following is also amenable to other imaging modalities.

BACKGROUND OF THE INVENTION

A computed tomography (CT) scanner generally includes an x-ray tube mounted on a rotatable gantry that rotates around an examination region about a z-axis. The x-ray tube emits radiation that traverses the examination region and a subject or object positioned therein. A detector array subtends an angular arc opposite the examination region from the x-ray tube, detects radiation that traverses the examination region, and generates a signal indicative thereof. A reconstructor processes the signal and reconstructs volumetric image data indicative thereof the examination region.

The detector array has included a plurality of detector modules. Each detector module has included a plurality of photodiode array tiles bonded to a module substrate. Each photodiode array tile has included a scintillator optically coupled on a radiation receiving side and an ASIC bonded to the other side. To construct such a detector module, the ASIC is coupled to the photodiode array tile, and then the photodiode array tile (with the ASIC mounted thereon) is coupled to the module substrate. The scintillator is coupled to the photodiode array tile.

With one configuration, the ASIC is soldered to the photodiode array tile, and then the photodiode array tile with the ASIC is soldered to the module substrate. The soldering has been achieved through reflow soldering using a reflow oven. Unfortunately, the heat used to solder the photodiode array tile with the ASIC to the module substrate may compromise the solder bond between the photodiode array tile and the ASIC. In view of at least the above, there is an unresolved need for other approaches to combine the photodiode array tile, the ASIC and the module substrate.

SUMMARY OF THE INVENTION

Aspects described herein address the above-referenced problems and/or others.

In one aspect, a module assembly device is configured for assembling a module assembly for a detector array of an imaging system. The module assembly device includes a module substrate, an ASIC, a photo-detector array tile, and a scintillator. The module assembly device includes a base having a long axis. The module assembly device further includes a first surface of the base and side walls protruding perpendicular up from the first surface and extending in a direction of the long axis along at least two sides of the base. The first surface and side walls form a recess configured to receive the module substrate on the surface and within the side walls. The module assembly device further includes protrusions protruding from the side walls in a direction of the side walls. The protrusions and side walls interface forming a ledge which serves as a photo-detector array tile support configured to receive the photo-detector array tile over the ASIC and the module substrate.

In another aspect, a method produces an imaging system detector array module assembly with a module assembly device. The module assembly device includes a base with a recess having a surface and side walls protruding therefrom, and a photo-detector array tile support extending from the side walls. The method includes receiving a module substrate on the surface of the assembly device, the module substrate including an opening. The method further includes receiving an ASIC on the surface through the opening, wherein the ASIC includes a first solder on a side facing away from the surface. The method further includes receiving a photo-detector array tile over the module substrate and the ASIC, wherein the photo-detector array tile includes a second solder in a first region of a side facing the module substrate and pads in a second region of the module substrate. The method further includes concurrently reflowing the first and second solders to concurrently bond the ASIC to the photo-detector array tile and the photo-detector array tile to the module substrate, which produces the module assembly.

In another aspect, a method produces an imaging system detector array module assembly with a module assembly device. The module assembly device includes a base with a recess having a first surface and side walls protruding therefrom, a photo-detector array tile support extending from the side walls, and a heat sink. The method includes receiving a module substrate on the surface of the assembly device, the module substrate including an opening. The method further includes receiving a photo-detector array tile with an ASIC mounted thereto, wherein the photo-detector array tile is received over the module substrate with the ASIC in the opening above the heat sink of the module assembly device, and the photo-detector array tile includes a solder in a region of a side facing the module substrate. The method further includes applying heat to the module assembly device. The method further includes concurrently, removing heat from a bond between the photo-detector array tile and the ASIC with the heat sink and reflowing the solder to bond the photo-detector array tile to the module substrate, which produces the module assembly.

In another aspect, a method produces an imaging system detector array module assembly with a module assembly device. The module assembly device includes a base with a recess having a first surface and side walls protruding therefrom, and a photo-detector array tile support extending from the side walls. The method includes receiving a module substrate on the surface of the assembly device, the module substrate including a recess and a heat sink disposed under the recess. The method further includes receiving a photo-detector array tile with an ASIC mounted thereto, wherein the photo-detector array tile is received over the module substrate with the ASIC in the recess, and the photo-detector array tile includes a solder in a region of a side facing the module substrate. The method further includes applying heat to the module assembly device. The method further includes concurrently, removing heat from a bond between the photo-detector array tile and the ASIC with the heat sink of the module substrate and reflowing the solder to bond the photo-detector array tile to the module substrate, which produces the module assembly.

In another aspect, an imaging system includes a detector array with a plurality of module assemblies. Each module assembly includes a module substrate, a plurality of photo-detector array tiles bonded to the module substrate, and a different ASIC bonded to each photo-detector array tile between the photo-detector array and the module substrate. One of: a module assembly includes concurrently formed solder bonds between an ASIC and a photo-detector array and the photo-detector array tile and the module substrate, or a module assembly includes sequentially formed solder bonds between an ASIC and a photo-detector array tile and then between the photo-detector array tile and the module substrate with heat removed from the ASIC/photo-detector array tile bond.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIGS. 4-6 schematically illustrate a top down, a first cross-sectional and a second different cross-sectional view of an example module assembly device.

FIGS. 7-15 schematically illustrate assembly of the module assembly of FIG. 2 using the module assembly device of FIGS. 4-6.

FIGS. 16-21 schematically illustrate assembly of the module assembly of FIG. 3 using the module assembly device of FIGS. 4-6.

FIGS. 22-24 schematically illustrate a top down, a first cross-sectional and a second different cross-sectional view of another example module assembly device.

FIGS. 25-30 schematically illustrate assembly of the module assembly of FIG. 2 using the module assembly device of FIGS. 16-18.

DETAILED DESCRIPTION OF EMBODIMENTS

A method and apparatus is disclosed which, in one non-limiting instance, overcomes simultaneously assembling components of tile detectors and modules as well as assembling them in steps so as to not unsolder soldered components in previous assembly steps and to overcome thermal sensitivity issues of scintillators during soldering assembly steps, thus providing a new generation of integrated CT detector modules.

Figure 1:
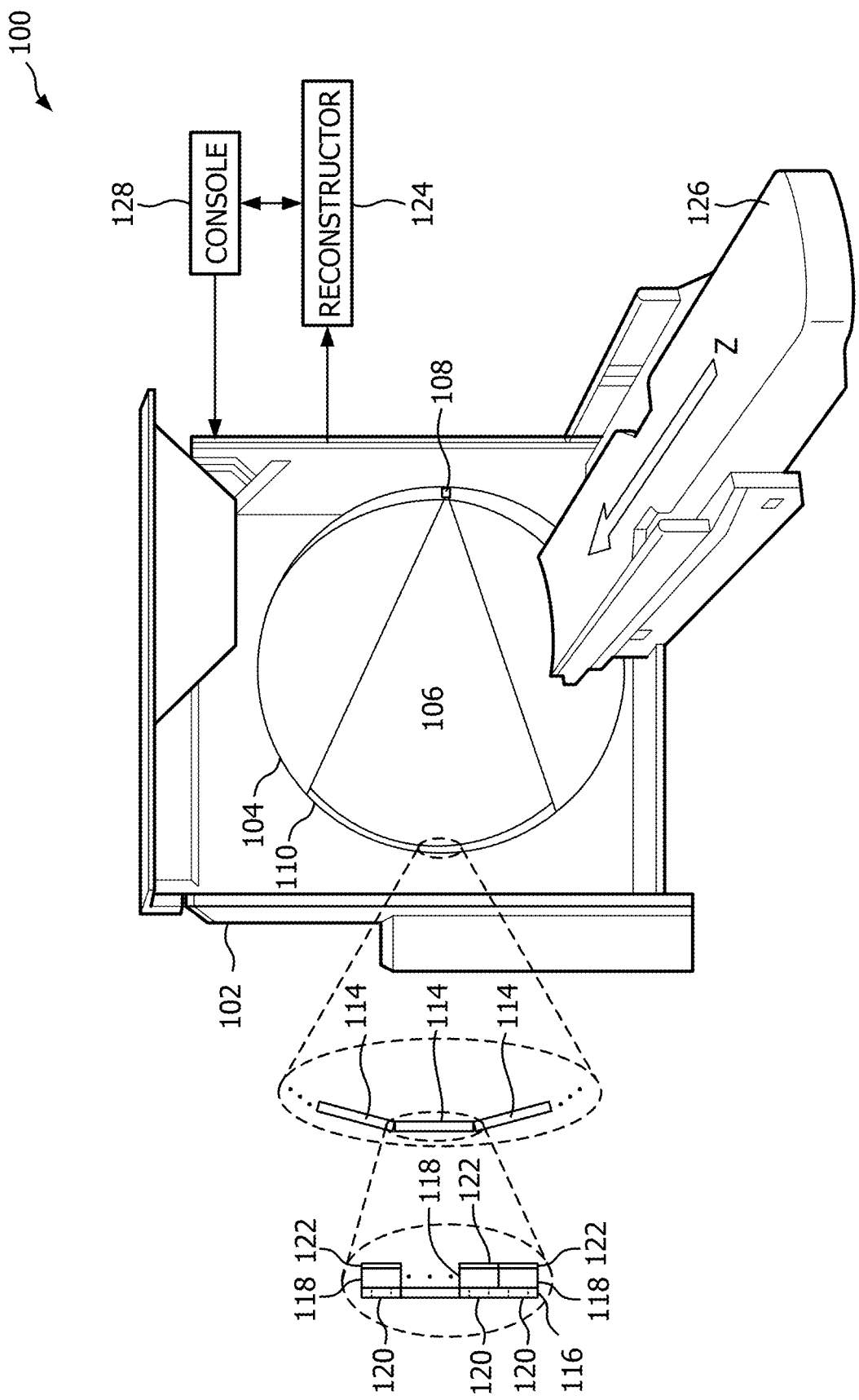
FIG. 1 schematically illustrates an example imaging system with a detector array that includes a plurality of module assemblies, each including a module substrate, a photo-detector array, an ASIC and a scintillator.

Initially referring to FIG. 1, an imaging system 100, such as a computed tomography (CT) scanner, is illustrated. The imaging system 100 includes a generally stationary gantry 102 and a rotating gantry 104. The rotating gantry 104 is rotatably supported by the stationary gantry 102 and rotates around an examination region 106 about a longitudinal or z-axis ("Z"). A radiation source 108, such as an x-ray tube, is supported by and rotates with the rotating gantry 104, and emits radiation.

A radiation sensitive detector array 110 subtends an angular arc opposite the radiation source 108 across the examination region 106, detects radiation traversing the examination region 106 and generates and outputs a signal indicative thereof. The radiation sensitive detector array 110 includes at least one row of module assemblies 114. In the illustrated example, the module assemblies 114 are sequentially aligned along a long axis of the detector array 110, arranged end to end in the x/y plane.

Each module assembly 114 includes a module substrate 116. A plurality of photo-detector array tiles 118 are physically and electrically coupled to the module substrate 116. A different electronic circuit 120 (e.g., an application specific integrated chip (ASIC), etc.) is physically and electrically coupled to a first side of each of the plurality of photo-detector array tiles 118. One or more scintillators 122 are physically and optically coupled to a second side (which opposes the first side) of the plurality of photo-detector array tiles 118.

As described in greater detail below, a module assembly 114 can be produced by concurrently reflowing solder disposed between the photo-detector array tiles 118 and the ASICs 120 and solder disposed between the photo-detector array tiles 118 and the module substrate 116, or by reflowing solder disposed between the photo-detector array tiles 118 with the ASICs 120 already bonded thereto and the module substrate 116, while mitigating compromising the bond between the photo-detector array tiles 118 and the ASICs 120.

A reconstructor 124 reconstructs the signal output by the detector array 110 and generates volumetric three-dimensional image data. A subject support 126, such as a couch, supports a subject or object in the examination region 106. A computing system serves as an operator console 128, which includes human readable output devices such as a display and/or printer and input devices such as a keyboard and/or mouse. Software resident on the console 128 allows the operator to control an operation of the imaging system 100, including initiating scanning, etc.

Figure 2:
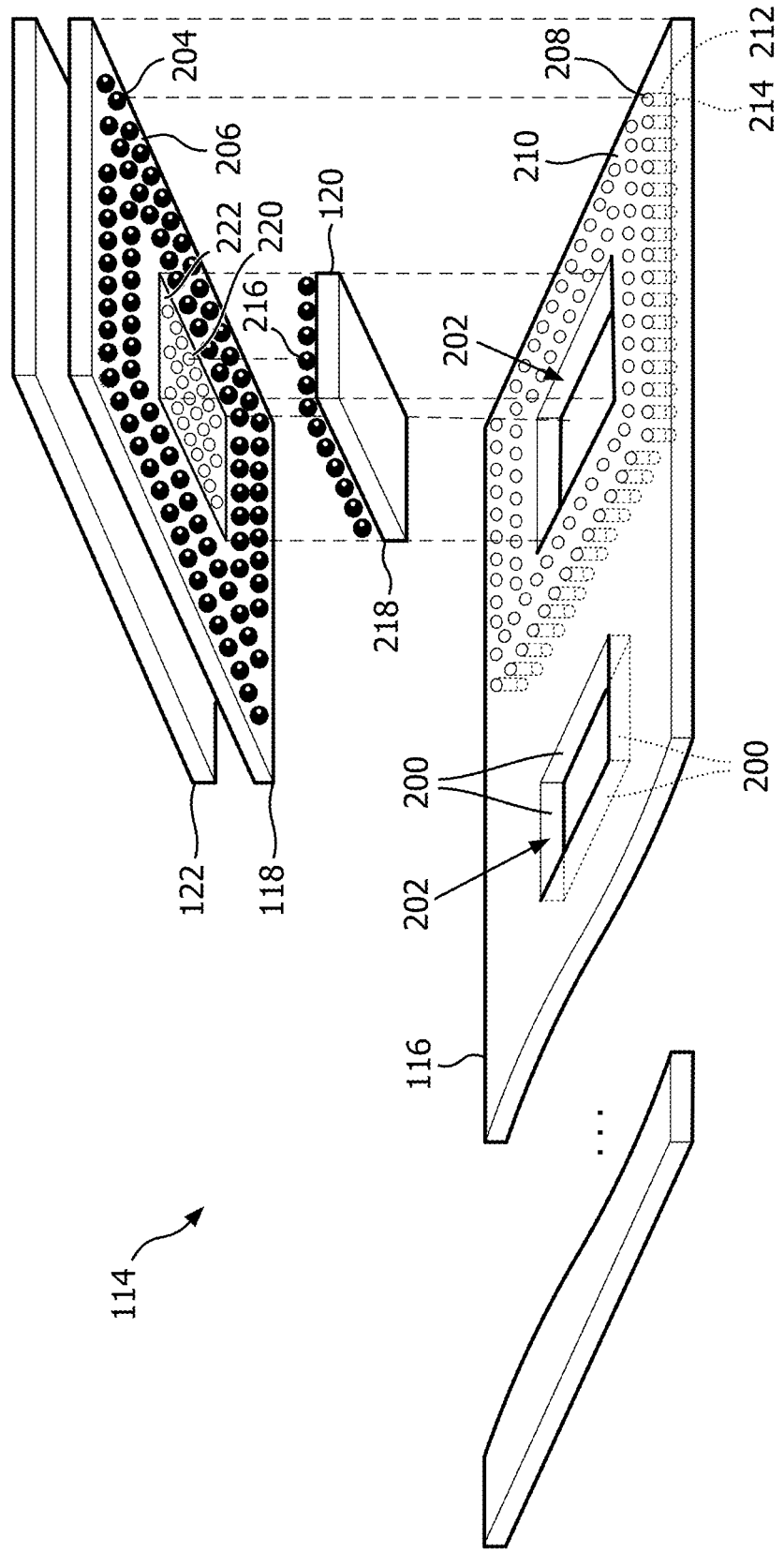
FIG. 2 schematically illustrates an example module assembly in which the ASIC is disposed in an opening of the module substrate.

FIG. 2 schematically shows an exploded view of a non-limiting example of a module assembly 114 in connection with a single ASIC/tile/scintillator unit 120/118/122.

The illustrated module substrate 116 includes a plurality of openings 202, which extend completely through the module substrate 116, bound by walls 200, which extend along a depth of the module substrate 116. An opening 202 has a geometry which is larger than a geometry of an ASIC 120, which sits inside of the opening 202. The photo-detector array tile 118 is shown with solder paste and/or solder balls 204 (also referred to herein as solder 204) on a region 206. The module substrate 116 is shown with corresponding pads 208 on a region 210. The solder 204 bonds the photo-detector array tile 118 to the module substrate 116.

Electrically conductive pathways (e.g., through hole vias) 212 electrically connect the pads 208 to electrically conductive contacts 214 on an opposing side of the module substrate 116. The ASIC 120 is shown with solder paste and/or solder balls 216 (also referred to herein as solder 216) on a region 218. The photo-detector array tile 118 is shown with corresponding pads 220 on a region 222. The solder 216 bonds the ASIC 120 to the photo-detector array tile 118. A module substrate 116 may be configured for 1, 2, 4, 8, 10, etc. ASIC/tile/scintillator units 120/118/122. One or more discrete electrical component can be soldered to the opposing side of the module substrate 116.

Figure 3:
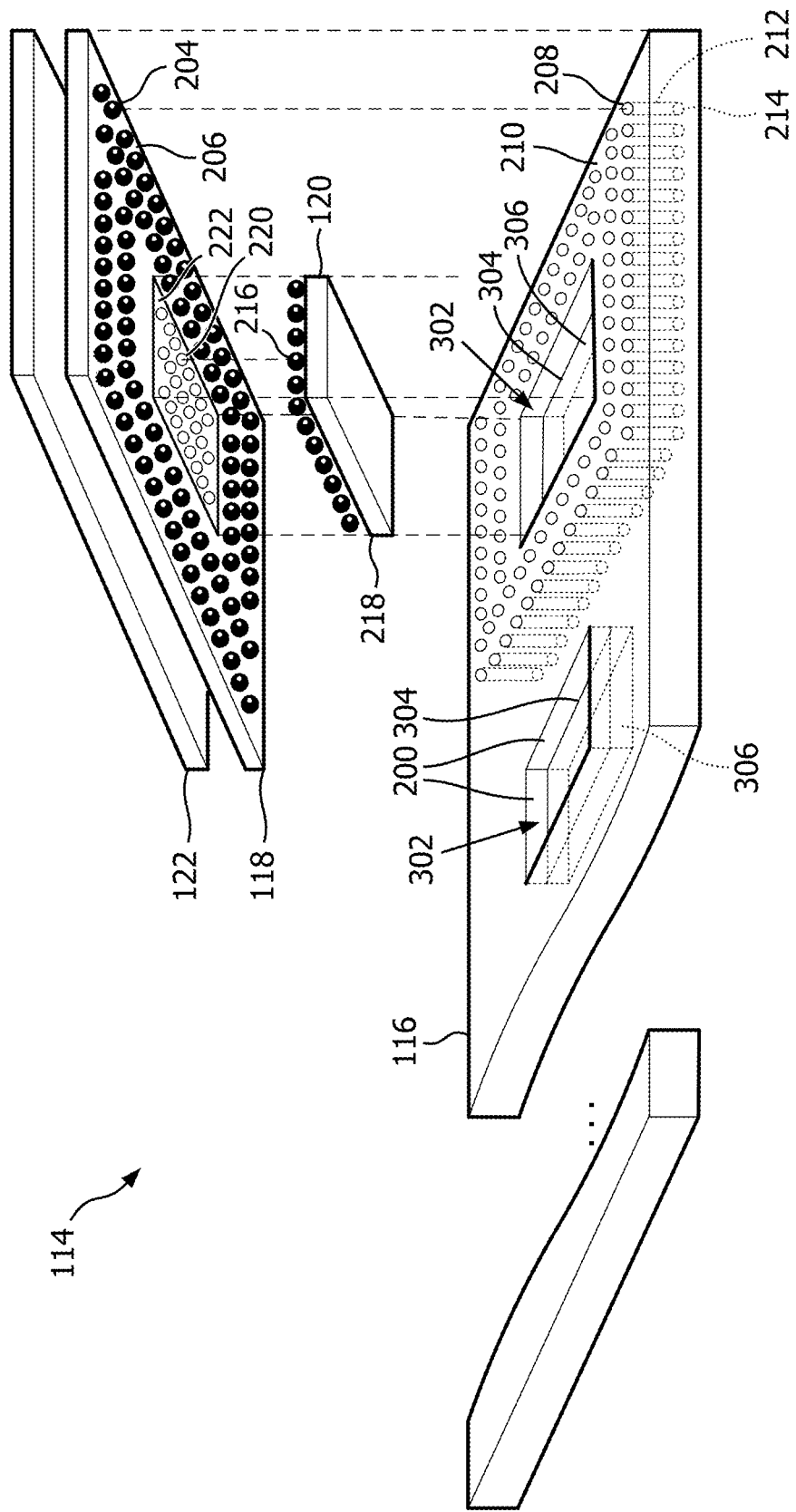
FIG. 3 schematically illustrates another example module assembly in which the ASIC is disposed in a recess of the module substrate.

FIG. 3 schematically illustrates a variation of FIG. 2 likewise showing an exploded view of a non-limiting example of a module assembly 114 in connection with a single ASIC/tile/scintillator unit 120/118/122. The reference numerals 200, 202, 204, 206, 208, 210, 212, 214, 216, 218, 220, and 222 are as described in FIG. 2.

In this variation, the module substrate 116 includes a plurality of recesses 302 instead of the opening 202. The recesses 302 extend, but not completely through, the depth of the module substrate 116, e.g., to surfaces 304, which bond, along with the walls 200, the recesses 302. Furthermore, the module substrate 116 includes a heat sink 306 disposed below each of the recesses 302. In this example, the heat sinks 306 are part of module substrate 116. Likewise, one or more discrete electrical component can be soldered to the opposing side of the module substrate 116.

With the configurations of FIGS. 3 and 4, individual ASICS 120, tiles 118, and/or scintillators 122 can be removed from a module substrate 116 of a module assembly 114 without affecting other ASICS 120, tiles 118, and/or scintillators 122 bonded to the module substrate 116. In one instance, this allows for localizing and replacing one or more of an ASIC 120, a tile 118, and/or a scintillator 122, for example, to replace a faulty and/or underperforming ASIC 120, tile 118, and/or scintillator 122. In one instance, this is achieve by applying heat to the ASIC(s) 120, tile(s) 118, and/or scintillator(s) 122 of interest and no other ASICs 120, tiles 118, and/or scintillator 122.

FIGS. 4-6 show example of a sub-portion of the module assembly device 402. FIG. 4 depicts a top down view, FIG. 5 depicts a cross sectional view along line A-A, and FIG. 6 depicts a cross sectional view along line B-B.

In this example, the module assembly device 402 is configured for assembling the module assembly of FIG. 2 with concurrent reflow of the solders 204 and 216 or reflow of only the solder 204.

The module assembly device 402 includes a base 400 having a long axis 401. The module assembly device 402 further includes a surface 406 and side walls 408 which extend along a direction of the long axis 401 on at least two sides of the surface 406. The side walls 408 have a non-zero height which extends perpendicularly up from the surface 406. The surface 406 and side walls 408 form a recess 404 configured to receive a module substrate 116.

The side walls 408 include protrusions 403 that extend up therefrom in the same direction as the side walls 408. The side walls 408 have a first thickness, and the protrusions 403 have a second thickness. The first thickness is greater than the second thickness. This offset between the first and second thicknesses forms a ledge, which is configured to receive photo-detector array tile 118 and serves as a photo-detector array tile support 410.

FIGS. 7-15 illustrate assembly of the module assembly 114 of FIG. 2 with the module assembly device 402 of FIGS. 4-6 with concurrent reflow of the solders 204 and 216. The reference numerals 400, 401, 402, 403, 404, 406, 408 and 410 are as described in FIG. 4.

Figure 10:
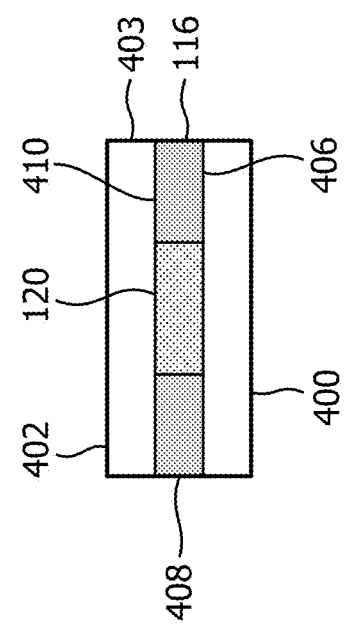
Figure 11:
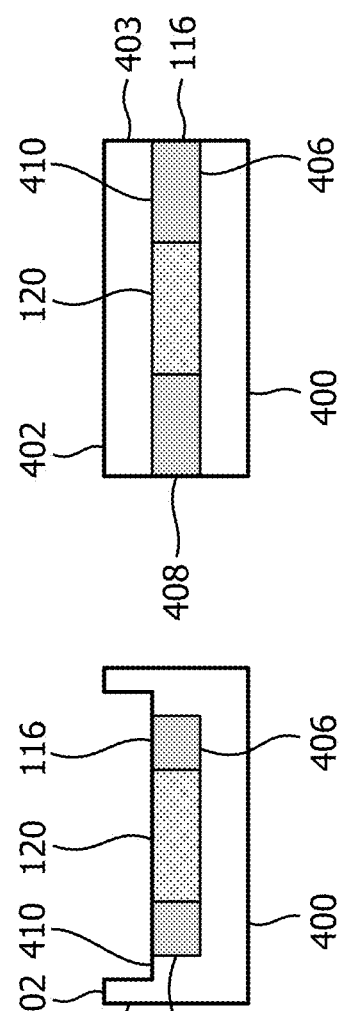
Figure 12:
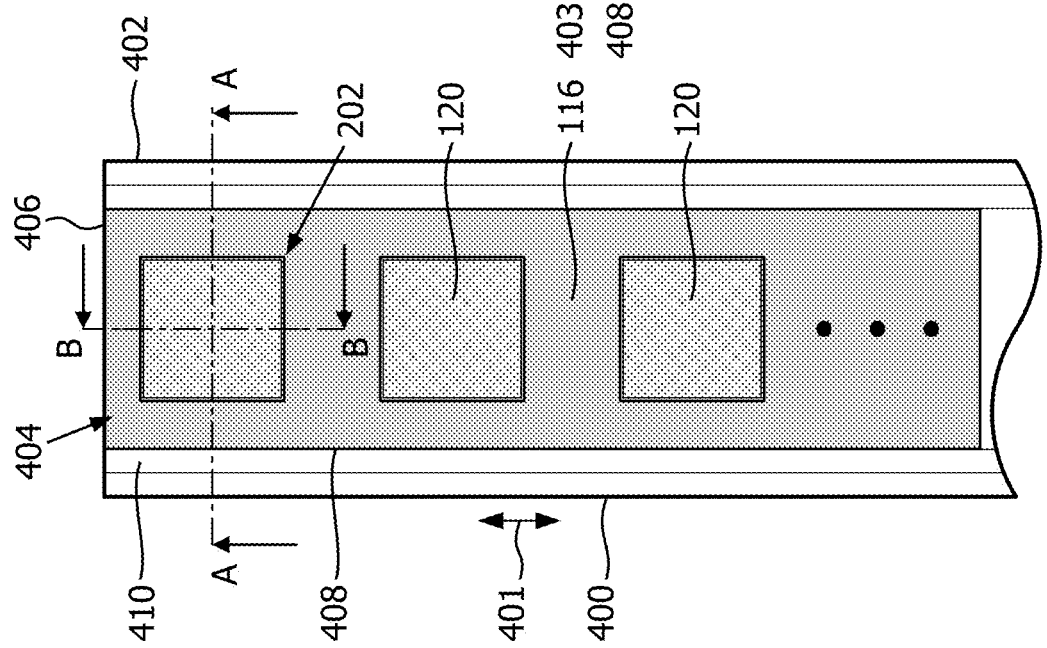

FIGS. 7-9 show the module assembly device 402 with a module substrate 116 installed in the recess 404. The module substrate 116 rests on the first surface 406. FIGS. 10-12 show the assembly device 402 with ASICs 120 installed in the openings 202 of the module substrate 116. FIGS. 13-15 show the assembly device 402 with photo-detector arrays tiles 118 installed on the photo-detector array tile support 410 over the module substrate 116 and the ASICs 120.

The module assembly device 402, after installing the module substrate 116, the ASICs 120, and the photo-detector arrays tiles 118, is heated, e.g., placed in a reflow oven, etc. The reflow oven is operated to bring the ambient temperature therein to a predetermined temperature, e.g., a melting temperature of the solders 204 and 216. Once the solders 204 and 216 reach the predetermined temperature, the solders 204 and 216 melt, concurrently bonding the ASICs 120 to the photo-detector arrays tiles 118 and the photo-detector arrays tiles 118 to the module substrate 116.

FIGS. 16-21 illustrate assembly of a module assembly 114 of FIG. 3 with the module assembly device 402 of FIGS. 4-6 with reflow of only the solder 204. The reference numerals 400, 401, 402, 403, 404, 406, 408 and 410 are as described in FIG. 4.

FIGS. 16-18 show the module assembly device 402 with a module substrate 116 installed in the recess 404. The module substrate 116 rests on the first surface 406. FIGS. 19-21 show the module assembly device 402 with photo-detector array tiles 118 with ASICs 120 already bonded thereto installed on photo-detector array tile support 410 over the module substrate 116 with the ASICs 120 in the recesses 404. The ASICs 120 are in thermal contact with the heat sinks 306.

In this example, once the heat in the reflow oven causes the solder 204 to reach the predetermined temperature, the solder 204 melts, bonding the photo-detector arrays tiles 118 to the module substrate 116. The heat sinks 306 draw heat away from the ASICs 120, preventing the solder 216 between the photo-detector arrays tiles 118 from melting and hence mitigating compromising the bond between photo-detector arrays tiles 118 and the ASICs 120.

FIGS. 22-24 show another example of a sub-portion of the module assembly device 402. FIG. 22 depicts a top down view, FIG. 23 depicts a cross sectional view along line A-A, and FIG. 24 depicts a cross sectional view along line B-B. In this example, the module assembly device 402 is configured for assembling the module assembly of FIG. 2 for reflowing only the solder 204.

The illustrated module assembly device 402 is substantially similar to that described in connection with FIGS. 4-6, except that in this configuration the module assembly device 402 further includes heat sinks 2202. The reference numerals 400, 401, 402, 403, 404, 406, 408 and 410 are as described in FIG. 4.

In the illustrated example, the heat sinks 2202 are integrated in and are part of the module assembly device 402. A region above a heat sink 2202 serves as an ASIC receiving region. In a variation, the heat sinks 2202 are separated components that install in the module assembly device 402. Furthermore, the illustrated heat sinks 2202 extend through the entire depth of the module substrate 116 in the recess 404. In a variation, the heat sinks 2202 may extend through only a sub-portion of the depth of the module substrate 116 in the recess 404.

In general, the heat sinks 2202 are disposed so as to be in thermal communication or make thermally conductive contact with at least a predetermined sub-portion of an installed module substrate 116. Furthermore, the illustrated heat sinks 2202 are shown as single element heat sinks 2202. However, it is to be appreciated that at least one of the heat sinks 2202 may include a plurality of individual sub-heat sinks (e.g., a plurality of thermally conductive standoffs, etc.) that together forms the heat sink 2202.

FIGS. 25-30 illustrate assembly of the module assembly 114 of FIG. 2 with the module assembly device 402 of FIGS. 22-24. The module assembly 114 of FIG. 3 can be similarly assembled with the module assembly device 402 of FIGS. 22-24. The reference numerals 400, 401, 402, 403, 404, 406, 408 and 410 are as described in FIG. 4.

FIGS. 25-27 show the module assembly device 402 with a module substrate 116 installed in the recess 404. The module substrate 116 rests on the first surface 406 with the heat sinks 2202 aligned with the openings 202. FIGS. 28-30 show the module assembly device 402 with photo-detector arrays tile 118 with ASICs 120 already bonded thereto installed on photo-detector array tile support 410 over the module substrate 116 with the ASICs 120 in the openings 202. The ASICs 120 are in thermal contact with the heat sinks 2202.

In this example, once the heat in the reflow oven causes the solder 204 to reach the predetermined temperature, the solder 204 melts, bonding the photo-detector arrays tiles 118 to the module substrate 116. The heat sinks 2202 draw heat away from the ASICs 120, preventing the solder 216 between the photo-detector arrays tiles 118 from melting and hence mitigating compromising the bond between photo-detector arrays tiles 118 and the ASICs 120.

Figure 31:
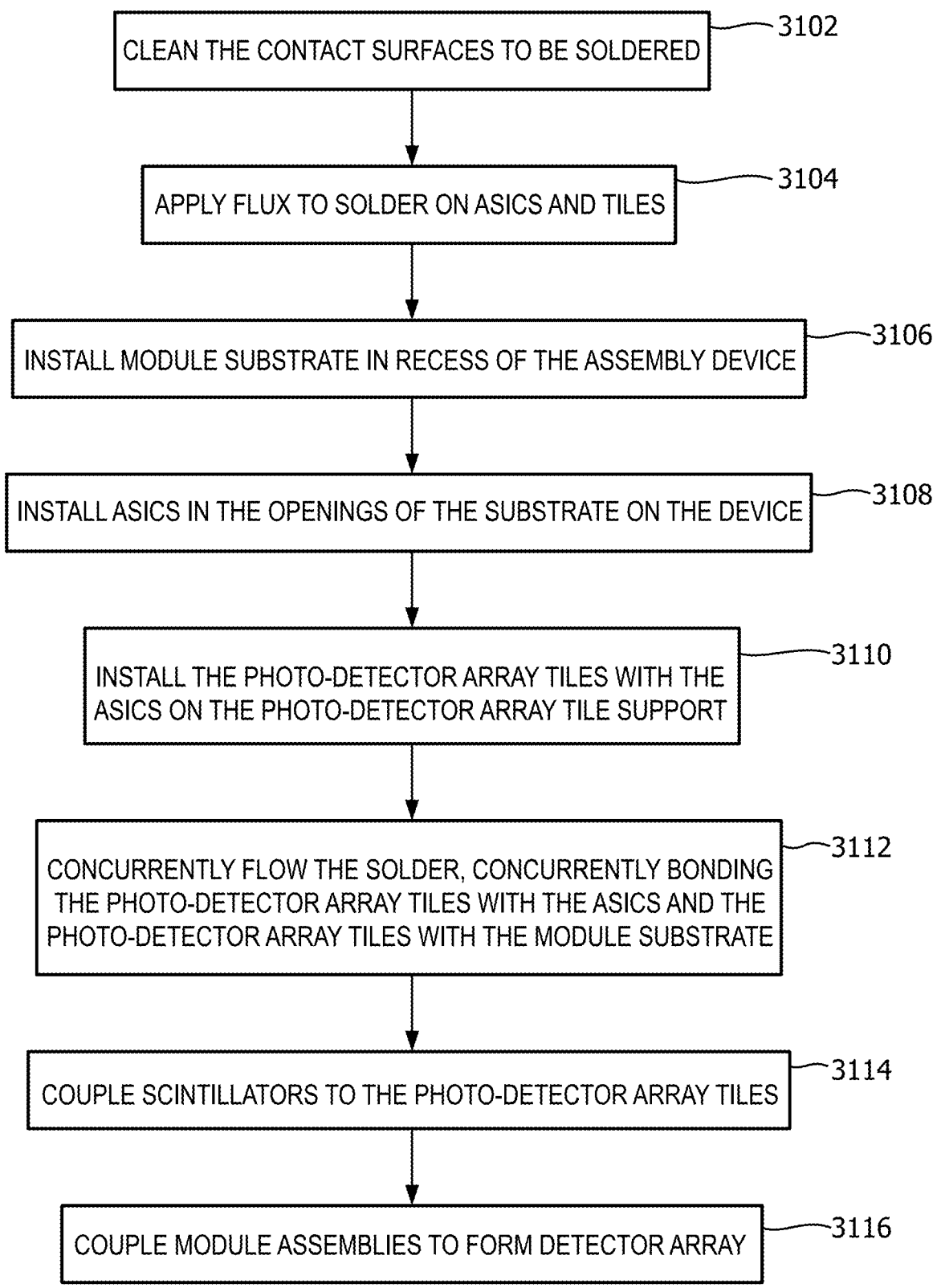
FIG. 31 illustrates an example method for assembling the module assembly of FIG. 2 with the module assembly device of FIGS. 4-6.

FIG. 31 illustrates a method for producing a module assembly 114 of FIG. 2 with the assembly device of FIGS. 4-6.

It is to be appreciated that the ordering of the acts in the methods described herein is not limiting. As such, other orderings are contemplated herein. In addition, one or more acts may be omitted and/or one or more additional acts may be included.

At 3102, contact surfaces to be soldered are cleaned.

At 3104, flux is applied to the solder 216 on the ASICs 120 and the solder 204 on the photo-detector array tiles 118.

At 3106, a module substrate 116 is installed in the recess 404 of the assembly device 402.

At 3108, the ASICs 120 are installed in the openings 202 of the module substrate 116 with the solder 216 facing away from the module substrate 116.

At 3110, the photo-detector arrays tiles 118 are installed on the photo-detector array tile support 410 over the module substrate 116 and the ASICs 120.

At 3112, the solder pastes 204 and 216 are concurrently reflowed, concurrently bonding the ASICs 120 to the photo-detector array tiles 118 and the photo-detector arrays tiles 118 to the module substrate 116.

At 3114, the scintillator 122 is physically and optically coupled to the photo-detector arrays tiles 118, e.g., using an optical adhesive or the like, creating the module assembly 114.

At 316, a plurality of module assemblies 114 is coupled to form the detector array 110.

Figure 32:
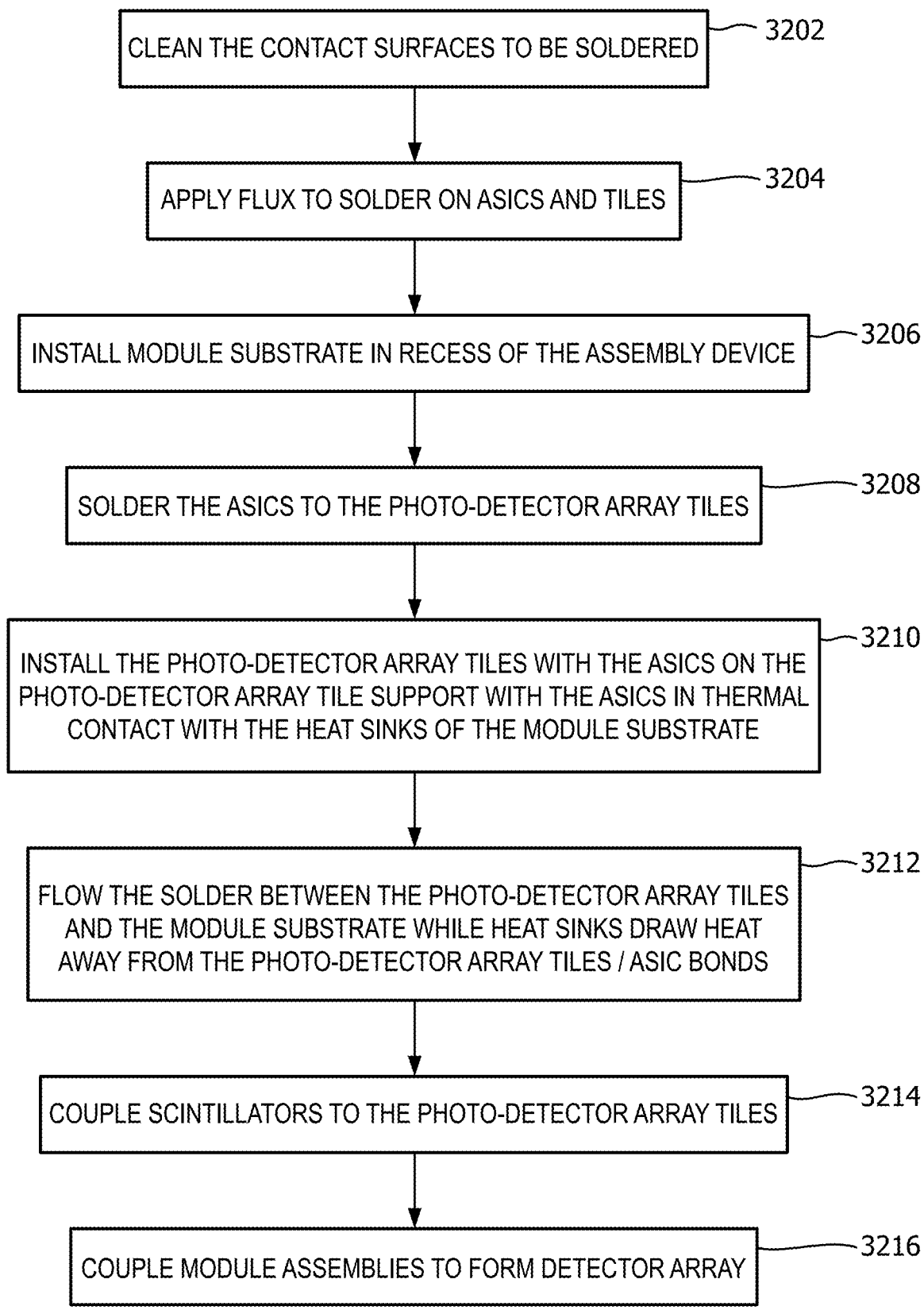
FIG. 32 illustrates an example method for assembling the module assembly of FIG. 3 with the module assembly device of FIGS. 4-6.

FIG. 32 illustrates a method for producing a module assembly 114 of FIG. 3 with the assembly device of FIGS. 4-6.

It is to be appreciated that the ordering of the acts in the methods described herein is not limiting. As such, other orderings are contemplated herein. In addition, one or more acts may be omitted and/or one or more additional acts may be included.

At 3202, contact surfaces to be soldered are cleaned.

At 3204, flux is applied to the solder 216 on the ASICs 120 and the solder 204 on the photo-detector array tiles 118.

At 3206, a module substrate 116 is installed in the recess 404 of the module assembly device 402.

At 3208, the ASICs 120 are mounted to the photo-detector arrays tiles 118 by reflowing the solder 216.

At 3210, the photo-detector arrays tiles 118 with the ASICs 120 are installed on the photo-detector array tile support 410 with the ASICs 120 in the recesses 302 and in thermal contact with the heat sinks 306 of the module substrate 116.

At 3212, the solder 204 is reflowed, bonding the photo-detector arrays tiles 118 to the module substrate 116, while the heat sinks 306 draw heat away from the solder 216 between bonding the photo-detector arrays tiles 118 and the ASICS 120.

At 3214, the scintillator 122 is physically and optically coupled to the photo-detector arrays tiles 118, e.g., using an optical adhesive or the like, creating the module assembly 114.

At 3216, a plurality of module assemblies 114 is coupled to form the detector array 110.

Figure 33:
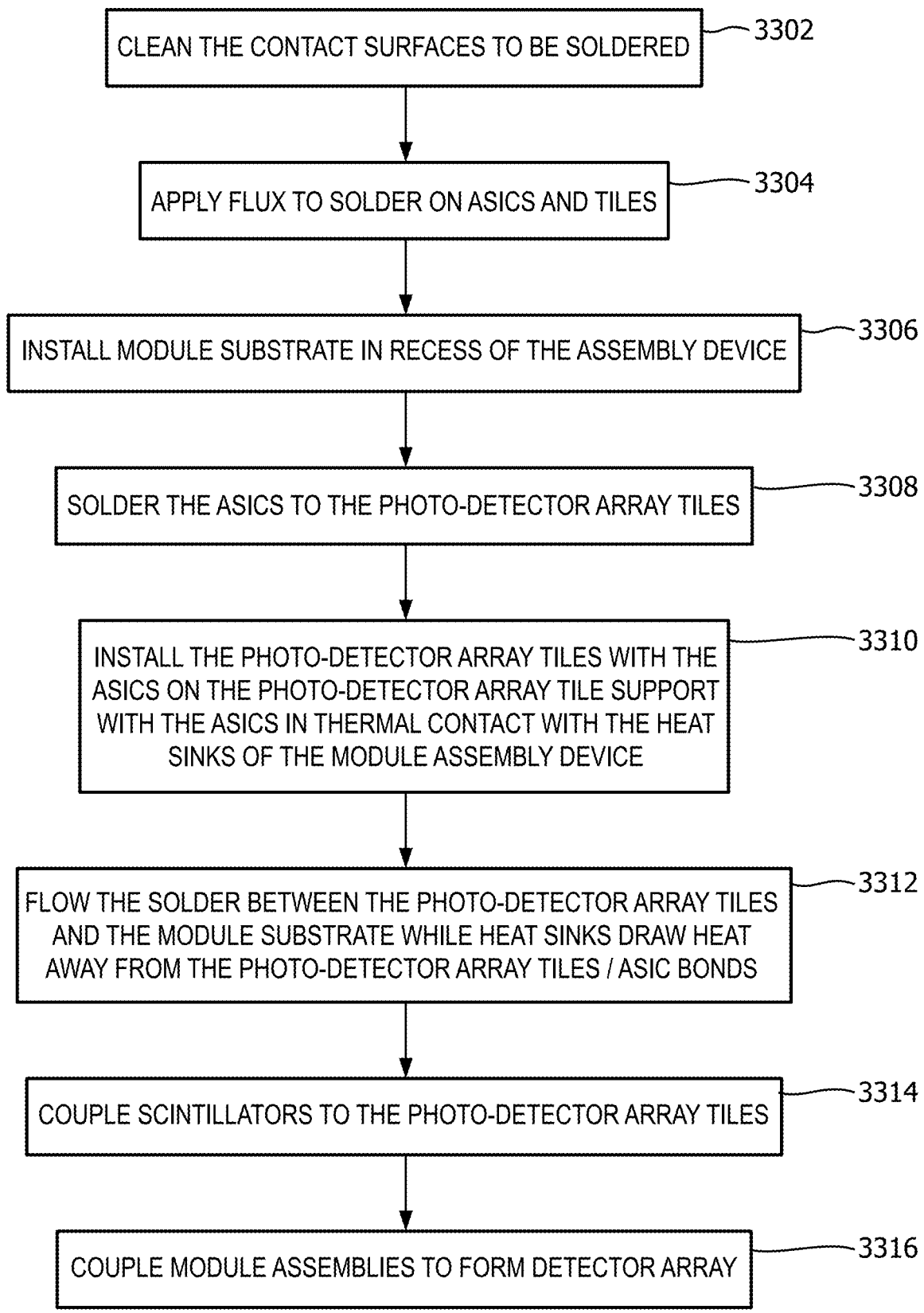
FIG. 33 illustrates an example method for assembling the module assembly of FIG. 2 with the module assembly device of FIGS. 22-24.

FIG. 33 illustrates a method for producing a module assembly 114 of FIG. 2 with the assembly device of FIGS. 22-24.

It is to be appreciated that the ordering of the acts in the methods described herein is not limiting. As such, other orderings are contemplated herein. In addition, one or more acts may be omitted and/or one or more additional acts may be included.

At 3202, contact surfaces to be soldered are cleaned.

At 3204, flux is applied to the solder 216 on the ASICs 120 and the solder 204 on the photo-detector array tiles 118.

At 3306, a module substrate 116 is installed in the recess 404 of the module assembly device 402.

At 3308, the ASICs 120 are mounted to the photo-detector arrays tiles 118 by reflowing the solder 216.

At 3310, the photo-detector arrays tiles 118 with the ASICs 120 are installed on the photo-detector array support 410 with the ASICs 120 in the openings 202 and in thermal contact with the heat sinks 2202 of the module assembly device 402.

At 3312, the solder 204 is reflowed, bonding the photo-detector arrays tiles 118 to the module substrate 116, while the heat sinks 2202 draw heat away from the solder 216 between bonding the photo-detector arrays tiles 118 and the ASICS 120.

At 3314, the scintillator 122 is physically and optically coupled to the photo-detector arrays tiles 118, e.g., using an optical adhesive or the like, creating the module assembly 114. Optionally, this act is performed prior to act 3102.

At 3316, a plurality of module assemblies 114 is coupled to form the detector array 110.

It is to be appreciated that the method of FIG. 33 can alternatively be utilized for producing a module assembly 114 of FIG. 3 with the assembly device of FIGS. 22-24. The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for producing an imaging system detector array module assembly with a module assembly device, wherein the module assembly device includes a base with a recess, the recess having a surface and side walls protruding from the surface, and a photo-detector array tile support extending from the side walls, the method comprising:
receiving, on the surface of the recess of the base of the module assembly device, a module substrate, the module substrate including an opening;
receiving, on the surface of the recess of the base of the module assembly device, an integrated circuit through the opening of the module substrate that has been received on the surface of the recess of the base, wherein the integrated circuit includes a first solder on a side facing away from the surface of the recess;
receiving, by the base of the module assembly device, a photo-detector array tile directly over the module substrate and the integrated circuit, wherein the photo-detector array tile includes a second solder in a first region of a side facing the module substrate and pads in a second region of the module substrate; and
concurrently reflowing the first and second solders to concurrently bond the integrated circuit to the photo-detector array tile and the photo-detector array tile to the module substrate, which produces the module assembly.

2. The method of claim 1, further comprising:
coupling, after reflowing the first and second solders, a scintillator to a radiation sensitive side of the photo-detector array tile facing away from the module substrate.

3. The method of claim 1, further comprising:
coupling, prior to receiving the photo-detector array tile, a scintillator to a radiation sensitive side of the photo-detector array tile facing away from the module substrate.

4. A method for producing an imaging system detector array module assembly with a module assembly device, wherein the module assembly device includes a base with a recess, the recess having a surface and side walls protruding from the surface, a photo-detector array tile support extending from the side walls, and a heat sink, the method comprising:
receiving, on the surface of the recess of the base of the module assembly device, a module substrate, the module substrate including an opening;
receiving, by the base of the module assembly device, a photo-detector array tile with an integrated circuit that is mounted to the photo-detector array tile, wherein the receiving of the photo-detector array tile comprises receiving the photo-detector array the directly over the module substrate during disposing of the integrated circuit in the opening of the module substrate above the heat sink of the module assembly device, and wherein the photo-detector array tile includes a solder in a region of a side facing the module substrate;
applying heat to the module assembly device; and
concurrently, removing heat from a bond between the photo-detector array tile and the integrated circuit with the heat sink and reflowing the solder to bond the photo-detector array tile to the module substrate, which produces the module assembly.

5. The method of claim 4, further comprising:
coupling, after reflowing the solder, a scintillator to a radiation sensitive side of the photo-detector array tile facing away from the module substrate.

6. The method of claim 4, further comprising:
coupling, prior to receiving the photo-detector array tile, a scintillator to a radiation sensitive side of the photo-detector array tile facing away from the module substrate.

7. A method for producing an imaging system detector array module assembly with a module assembly device, wherein the module assembly device includes a base with a recess, the recess having a surface and side walls protruding from the surface, and a photo-detector array tile support extending from the side walls, the method comprising:
receiving, on the surface of the recess of the base of the module assembly device, a module substrate, the module substrate including a recess and a heat sink disposed under the recess of the module substrate;
receiving, by the base of the module assembly device, a photo-detector array tile with an integrated circuit that is mounted to the photo-detector array tile, wherein the receiving of the photo-detector array tile comprises receiving the photo-detector array the directly over the module substrate during disposing of the integrated circuit in the recess of the substrate, and wherein the photo-detector array tile includes a solder in a region of a side facing the module substrate;
applying heat to the module assembly device; and
concurrently, removing heat from a bond between the photo-detector array tile and the integrated circuit with the heat sink of the module substrate and reflowing the solder to bond the photo-detector array tile to the module substrate, which produces the module assembly.

8. The method of claim 7, further comprising:
coupling, after reflowing the solder, a scintillator to a radiation sensitive side of the photo-detector array tile facing away from the module substrate.

9. The method of claim 7, further comprising:
coupling, prior to receiving the photo-detector array tile, a scintillator to a radiation sensitive side of the photo-detector array tile facing away from the module substrate.

10. The method of claim 1, wherein the module assembly device is configured for assembling the module assembly, wherein the base of the module assembly device comprises a long axis, wherein the side walls of the recess of the base of the module assembly device protrude perpendicular up from the surface of the recess of the base of the module assembly device and extend in a direction of the long axis along at least two sides of the base, wherein the module assembly device comprises protrusions protruding from the side walls in a direction of the side walls, the protrusions and side walls interface forming a ledge that servers as a photo-detector array tile support,
wherein the receiving, by the recess of the base of the module assembly device, of the module substrate comprises receiving the module substrate within the side walls recess of the module assembly device, and
wherein the receiving, by the base of the module assembly device, of the photo-detector array tile comprises receiving, by the ledge formed by the protrusions and the side walls interface, the photo-detector array tile directly over the module substrate and the integrated circuit.

11. The method of claim 4, wherein the module assembly device is configured for assembling the module assembly, wherein the base of the module assembly device comprises a long axis, wherein the side walls of the recess of the base of the module assembly device protrude perpendicular up from the surface of the recess of the base of the module assembly device and extend in a direction of the long axis along at least two sides of the base, wherein the module assembly device comprises protrusions protruding from the side walls in a direction of the side walls, the protrusions and side walls interface forming a ledge that servers as a photo-detector array tile support,
- wherein the receiving, by the recess of the base of the module assembly device, of the module substrate comprises receiving the module substrate within the side walls recess of the module assembly device, and
- wherein the receiving, by the base of the module assembly device, of the photo-detector array tile comprises receiving, by the ledge formed by the protrusions and the side walls interface, the photo-detector array tile directly over the module substrate with the integrated circuit.

12. The method of claim 7, wherein the module assembly device is configured for assembling the module assembly, wherein the base of the module assembly device comprises a long axis, wherein the side walls of the recess of the base of the module assembly device protrude perpendicular up from the surface of the recess of the base of the module assembly device and extend in a direction of the long axis along at least two sides of the base, wherein the module assembly device comprises protrusions protruding from the side walls in a direction of the side walls, the protrusions and side walls interface forming a ledge that servers as a photo-detector array tile support,
- wherein the receiving, by the recess of the base of the module assembly device, of the module substrate comprises receiving the module substrate within the side walls recess of the module assembly device, and
- wherein the receiving, by the base of the module assembly device, of the photo-detector array tile comprises receiving, by the ledge formed by the protrusions and the side walls interface, the photo-detector array tile directly over the module substrate with the integrated circuit.

\* \* \* \* \*